United States Patent
Prandi et al.

(10) Patent No.: US 10,349,988 B2
(45) Date of Patent: Jul. 16, 2019

(54) ORTHOPEDIC IMPLANT IN THE FORM OF A PLATE TO BE FIXED BETWEEN TWO BONE PARTS

(71) Applicant: Stryker European Holdings I, LLC, Kalamazoo, MI (US)

(72) Inventors: Bernard Prandi, Rennes (FR); Keith Wapner, Philadelphia, PA (US); Charles P. Wapner, Media, PA (US); Peter W. Wapner, Media, PA (US)

(73) Assignee: Stryker European Holdings I, LLC, Kalamazoo, MI (US)

(*) Notice: Subject to any disclaimer, the term of this patent is extended or adjusted under 35 U.S.C. 154(b) by 615 days.

(21) Appl. No.: 15/130,147

(22) Filed: Apr. 15, 2016

(65) Prior Publication Data

US 2016/0228164 A1 Aug. 11, 2016

Related U.S. Application Data

(63) Continuation of application No. 14/734,676, filed on Jun. 9, 2015, now Pat. No. 9,333,013, which is a
(Continued)

(30) Foreign Application Priority Data

Oct. 2, 2008 (FR) ..................... 08 56694

(51) Int. Cl.
*A61B 17/80* (2006.01)
*A61B 17/84* (2006.01)
*A61B 17/68* (2006.01)

(52) U.S. Cl.
CPC ...... *A61B 17/8014* (2013.01); *A61B 17/8004* (2013.01); *A61B 17/808* (2013.01);
(Continued)

(58) Field of Classification Search
CPC ....... A61B 17/80; A61B 17/84; A61B 17/808; A61B 17/8061; A61B 17/8057; A61B 17/846
See application file for complete search history.

(56) References Cited

U.S. PATENT DOCUMENTS 2,486,303 A 10/1949 Longfellow
3,528,085 A 9/1970 Reynolds
(Continued)

FOREIGN PATENT DOCUMENTS

DE 3027148 A1 12/1981
DE 8227727 U1 12/1982
(Continued)

OTHER PUBLICATIONS

European Search Report for Application No. 16185971 dated Feb. 9, 2017.
(Continued)

*Primary Examiner* — Christopher J Beccia
(74) *Attorney, Agent, or Firm* — Lerner, David, Littenberg, Krumholz & Mentlik, LLP

(57) ABSTRACT

The invention relates to a plate fixed between two bone parts by way of screws engaged in holes formed in the thickness of said plate. The plate comprises an angled member or rib which is inclined according to an angle of between about 30° and 60° in relation to the plane defined by the plate. The angled member or rib has a hole for engaging a screw and is located in the central part of the width, over a determined part of the length of the plate, so that the screw brings the two bone parts into a compressive position.

27 Claims, 2 Drawing Sheets

Related U.S. Application Data continuation of application No. 14/041,706, filed on Sep. 30, 2013, now Pat. No. 9,078,713, which is a continuation of application No. 12/918,071, filed as application No. PCT/FR2009/051879 on Oct. 2, 2009, now Pat. No. 8,556,946.

(52) U.S. Cl.
CPC ........ *A61B 17/809* (2013.01); *A61B 17/8052* (2013.01); *A61B 17/8057* (2013.01); *A61B 17/8061* (2013.01); *A61B 17/846* (2013.01); *A61B 2017/681* (2013.01)

(56) References Cited

U.S. PATENT DOCUMENTS

| | | | |
|---|---|---|---|
| 3,534,731 | A | 10/1970 | Muller |
| 3,552,389 | A | 1/1971 | Allgower et al. |
| 3,779,240 | A | 12/1973 | Kondo |
| RE28,841 | E | 6/1976 | Allgower et al. |
| 4,388,921 | A | 6/1983 | Sutter et al. |
| 4,408,601 | A | 10/1983 | Wenk |
| RE31,628 | E | 7/1984 | Allgower et al. |
| 4,493,317 | A | 1/1985 | Klaue |
| 4,503,737 | A | 3/1985 | DiGiovanni |
| 4,513,744 | A | 4/1985 | Klaue |
| 4,651,724 | A | 3/1987 | Berentey et al. |
| 4,800,874 | A | 1/1989 | David et al. |
| 4,957,496 | A | 9/1990 | Schmidt |
| 4,988,350 | A * | 1/1991 | Herzberg ............ A61B 17/746 606/65 |
| 5,105,690 | A | 4/1992 | Lazzara et al. |
| 5,304,180 | A | 4/1994 | Slocum |
| 5,347,894 | A | 9/1994 | Fischer |
| 5,487,741 | A | 1/1996 | Maruyama et al. |
| 5,662,655 | A | 9/1997 | Laboureau et al. |
| 5,667,510 | A | 9/1997 | Combs |
| 5,674,222 | A | 10/1997 | Berger et al. |
| 5,709,686 | A | 1/1998 | Talos et al. |
| 5,810,822 | A | 9/1998 | Mortier |
| 5,827,285 | A | 10/1998 | Bramlet |
| 5,853,413 | A | 12/1998 | Carter et al. |
| 5,904,684 | A | 5/1999 | Rooks |
| 5,931,839 | A | 8/1999 | Medoff |
| 6,146,382 | A | 11/2000 | Hurlbert |
| 6,183,475 | B1 | 2/2001 | Lester et al. |
| 6,348,052 | B1 | 2/2002 | Sammarco |
| 6,379,359 | B1 | 4/2002 | Dahners |
| 6,383,186 | B1 | 5/2002 | Michelson |
| 6,533,786 | B1 | 3/2003 | Needham et al. |
| 6,544,266 | B1 | 4/2003 | Roger et al. |
| 6,565,570 | B2 | 5/2003 | Sterett et al. |
| 6,576,018 | B1 | 6/2003 | Holt |
| 6,623,486 | B1 | 9/2003 | Weaver et al. |
| 6,626,907 | B2 | 9/2003 | Campbell et al. |
| 6,669,700 | B1 | 12/2003 | Farris et al. |
| 6,669,701 | B2 | 12/2003 | Steiner et al. |
| 6,692,503 | B2 | 2/2004 | Foley et al. |
| 6,712,820 | B2 | 3/2004 | Orbay |
| 6,719,759 | B2 | 4/2004 | Wagner et al. |
| 6,730,091 | B1 | 5/2004 | Pfefferle et al. |
| 6,764,489 | B2 | 7/2004 | Ferree |
| 6,960,211 | B1 | 11/2005 | Pfefferle et al. |
| 7,037,342 | B2 | 5/2006 | Nilsson et al. |
| 7,044,951 | B2 * | 5/2006 | Medoff ................ A61B 17/80 606/281 |
| 7,108,697 | B2 | 9/2006 | Mingozzi et al. |
| 7,137,987 | B2 | 11/2006 | Patterson et al. |
| 7,179,260 | B2 * | 2/2007 | Gerlach ............ A61B 17/8014 606/291 |
| 7,326,218 | B2 | 2/2008 | Sterett et al. |
| 7,341,589 | B2 | 3/2008 | Weaver et al. |
| 7,344,538 | B2 | 3/2008 | Myerson et al. |
| D587,370 | S | 2/2009 | Coillard-Lavirotte et al. |
| 7,491,220 | B2 | 2/2009 | Coughln |
| D596,294 | S | 7/2009 | Coillard-Lavirotte et al. |
| 7,695,472 | B2 | 4/2010 | Young |
| 7,766,948 | B1 | 8/2010 | Leung |
| 7,771,457 | B2 | 8/2010 | Kay et al. |
| D623,745 | S | 9/2010 | Kay et al. |
| 7,799,061 | B2 | 9/2010 | Kay et al. |
| 7,819,903 | B2 | 10/2010 | Fraser et al. |
| 7,857,836 | B2 | 12/2010 | Huebner et al. |
| 7,931,680 | B2 | 4/2011 | Myerson et al. |
| 8,080,010 | B2 | 12/2011 | Schulz et al. |
| 8,100,954 | B2 | 1/2012 | Kay et al. |
| 8,100,983 | B2 | 1/2012 | Schulte |
| 8,852,246 | B2 * | 10/2014 | Hansson ............ A61B 17/8061 606/281 |
| 2001/0011172 | A1 | 8/2001 | Orbay et al. |
| 2001/0047172 | A1 | 11/2001 | Foley et al. |
| 2002/0045901 | A1 | 4/2002 | Wagner et al. |
| 2002/0183752 | A1 | 12/2002 | Steiner et al. |
| 2003/0040748 | A1 * | 2/2003 | Aikins ............... A61B 17/1668 606/70 |
| 2003/0060827 | A1 | 3/2003 | Coughln |
| 2003/0195516 | A1 | 10/2003 | Sterett et al. |
| 2003/0199875 | A1 | 10/2003 | Mingozzi et al. |
| 2004/0059334 | A1 | 3/2004 | Weaver et al. |
| 2004/0092929 | A1 | 5/2004 | Zindrick |
| 2004/0093081 | A1 | 5/2004 | Nilsson et al. |
| 2004/0097950 | A1 | 5/2004 | Foley et al. |
| 2004/0167522 | A1 | 8/2004 | Niederberger et al. |
| 2004/0172028 | A1 | 9/2004 | Roger |
| 2004/0181228 | A1 | 9/2004 | Wagner et al. |
| 2004/0186477 | A1 | 9/2004 | Winquist et al. |
| 2004/0210234 | A1 | 10/2004 | Coillard-Lavirotte et al. |
| 2004/0214137 | A1 | 10/2004 | Walton |
| 2004/0236332 | A1 | 11/2004 | Frigg |
| 2005/0015089 | A1 | 1/2005 | Young et al. |
| 2005/0070904 | A1 | 3/2005 | Gerlach et al. |
| 2005/0080421 | A1 | 4/2005 | Weaver et al. |
| 2005/0085913 | A1 | 4/2005 | Fraser et al. |
| 2005/0090825 | A1 | 4/2005 | Pfefferle et al. |
| 2005/0171544 | A1 * | 8/2005 | Falkner, Jr. ......... A61B 17/1728 606/281 |
| 2005/0182408 | A1 | 8/2005 | Pfefferle et al. |
| 2005/0277937 | A1 | 12/2005 | Leung et al. |
| 2005/0277941 | A1 | 12/2005 | Trumble et al. |
| 2006/0004362 | A1 | 1/2006 | Patterson et al. |
| 2006/0015102 | A1 | 1/2006 | Toullec et al. |
| 2006/0058796 | A1 | 3/2006 | Hartdegen et al. |
| 2006/0106387 | A1 | 5/2006 | Fanger et al. |
| 2006/0122607 | A1 | 6/2006 | Kolb |
| 2006/0149261 | A1 | 7/2006 | Nilsson et al. |
| 2006/0173459 | A1 | 8/2006 | Kay et al. |
| 2006/0200145 | A1 | 9/2006 | Kay et al. |
| 2006/0235397 | A1 | 10/2006 | Sanders et al. |
| 2006/0241607 | A1 | 10/2006 | Myerson et al. |
| 2006/0241608 | A1 | 10/2006 | Myerson et al. |
| 2006/0241609 | A1 | 10/2006 | Myerson et al. |
| 2007/0142920 | A1 | 6/2007 | Niemi |
| 2007/0233106 | A1 | 10/2007 | Horan et al. |
| 2007/0270850 | A1 | 11/2007 | Geissler |
| 2008/0015593 | A1 | 1/2008 | Pfefferle et al. |
| 2008/0051791 | A1 | 2/2008 | Young et al. |
| 2008/0091197 | A1 | 4/2008 | Coughlin |
| 2008/0114360 | A1 | 5/2008 | Da Frota Carrera |
| 2008/0132960 | A1 | 6/2008 | Weaver et al. |
| 2008/0161860 | A1 | 7/2008 | Ahrens et al. |
| 2008/0208262 | A1 | 8/2008 | Butler et al. |
| 2008/0249572 | A1 * | 10/2008 | Tandon ............ A61B 17/8004 606/280 |
| 2008/0249573 | A1 | 10/2008 | Buhren et al. |
| 2009/0024173 | A1 | 1/2009 | Reis, Jr. |
| 2009/0036933 | A1 | 2/2009 | Dube et al. |
| 2009/0093849 | A1 | 4/2009 | Grabowski |
| 2009/0118769 | A1 | 5/2009 | Sixto, Jr. et al. |
| 2009/0198285 | A1 | 8/2009 | Raven, III |
| 2009/0210010 | A1 | 8/2009 | Strnad et al. |
| 2009/0210011 | A1 | 8/2009 | Den Hartog et al. |
| 2009/0210013 | A1 | 8/2009 | Kay et al. |
| 2009/0228048 | A1 | 9/2009 | Duncan et al. |

(56) References Cited

U.S. PATENT DOCUMENTS

| | | |
|---|---|---|
| 2009/0234359 A1 | 9/2009 | Onoue et al. |
| 2009/0275987 A1 | 11/2009 | Graham et al. |
| 2009/0306724 A1 | 12/2009 | Leither et al. |
| 2009/0312759 A1 | 12/2009 | Ducharme et al. |
| 2010/0016900 A1* | 1/2010 | Terres ............... A61B 17/8019 606/280 |
| 2010/0057214 A1 | 3/2010 | Graham et al. |
| 2010/0121324 A1 | 5/2010 | Tyber et al. |
| 2010/0121325 A1 | 5/2010 | Tyber et al. |
| 2010/0125300 A1 | 5/2010 | Blitz et al. |
| 2010/0160973 A1 | 6/2010 | Leung |
| 2010/0217328 A1 | 8/2010 | Terrill et al. |
| 2010/0256638 A1 | 10/2010 | Tyber et al. |
| 2010/0256639 A1 | 10/2010 | Tyber et al. |
| 2010/0274293 A1 | 10/2010 | Terrill et al. |
| 2010/0305618 A1 | 12/2010 | Kay et al. |
| 2010/0324556 A1 | 12/2010 | Tyber et al. |
| 2011/0004253 A1 | 1/2011 | Fraser et al. |
| 2011/0009866 A1 | 1/2011 | Johnson et al. |
| 2011/0046681 A1 | 2/2011 | Prandi et al. |
| 2011/0087229 A1 | 4/2011 | Kubiak et al. |
| 2011/0087295 A1 | 4/2011 | Kubiak et al. |
| 2011/0092981 A1 | 4/2011 | Ng et al. |
| 2011/0093017 A1 | 4/2011 | Prasad et al. |
| 2011/0093018 A1 | 4/2011 | Prasad et al. |
| 2011/0118739 A1 | 5/2011 | Tyber et al. |
| 2011/0125153 A1 | 5/2011 | Tyber et al. |
| 2011/0213367 A1 | 9/2011 | Tyber et al. |
| 2011/0218535 A1 | 9/2011 | Wang et al. |
| 2011/0230884 A1 | 9/2011 | Mantzaris et al. |
| 2011/0264148 A1 | 10/2011 | Prandi et al. |
| 2011/0306976 A1 | 12/2011 | Kubiak et al. |
| 2011/0306977 A1 | 12/2011 | Michel et al. |

FOREIGN PATENT DOCUMENTS

| | | |
|---|---|---|
| DE | 3630862 A1 | 3/1988 |
| EP | 0 705 572 A2 | 4/1996 |
| EP | 1707227 A2 | 10/2006 |
| EP | 1897509 A1 | 3/2008 |
| FR | 590290 B | 6/1925 |
| FR | 2362616 A1 | 3/1978 |
| FR | 2764183 A1 | 12/1998 |
| FR | 2846870 A1 | 5/2004 |
| FR | 2912895 A1 | 8/2008 |
| WO | 95016403 A1 | 6/1995 |
| WO | 9528887 A1 | 11/1995 |
| WO | 1996005778 A1 | 2/1996 |
| WO | 2002098306 A1 | 12/2002 |
| WO | 2007131287 A1 | 11/2007 |

OTHER PUBLICATIONS

Catalogue General 1987-1988, plaques d'osteosynthese, bone plates, Division of Pfzer Hospital Products Group, Bagneux, France.

Manual of Small Animal Fracture Repair and Management, Jan. 1, 1998, pp. 80-81.

Vitallium Screw-Plate-Systems of Prof. R. Judet, 12 pages, 1974, Howmedica International, Inc. Shannon Industrial Estate, Co. Clare, Ireland.

* cited by examiner

ORTHOPEDIC IMPLANT IN THE FORM OF A PLATE TO BE FIXED BETWEEN TWO BONE PARTS

CROSS-REFERENCE TO RELATED APPLICATIONS

This application is a continuation of U.S. application Ser. No. 14/734,676, filed Jun. 9, 2015, which is a continuation of U.S. application Ser. No. 14/041,706, filed Sep. 30, 2013 and now U.S. Pat. No. 9,078,713, which is a continuation of U.S. application Ser. No. 12/918,071, filed Oct. 29, 2010 and now U.S. Pat. No. 8,556,946, which is a national phase entry under 35 U.S.C. § 371 of International Application No. PCT/FR2009/051879, filed Oct. 2, 2009, published in French, which claims priority from French Patent Application No. 0856694, filed Oct. 2, 2008, all of which are incorporated herein by reference in their entireties.

BACKGROUND OF THE INVENTION

The invention relates to the technical field of orthopedic implants.

More particularly, the invention relates to a plate for arthrodesis or osteosynthesis adapted to be fixed between two bone parts.

In a manner known to one having ordinary skill in the art, this type of plate generally has holes for engaging screws, allowing arthrodesis between two bones or osteosynthesis between two bone fragments. This is, for example, the case for bones of the hand or foot, without however excluding other applications, particularly in the field of the spine. Depending on the pathology to be treated, these plates can have a general rectilinear or other geometric shapes.

From this state of the art, one of the objects the invention proposes to attain is to improve, in a sure and efficient manner, compression in a precise direction between the bone parts subjected to the plate.

To attain the given object to enhance the compression between the two relative bone parts, according to the invention, the plate has a formation that orients at least one screw at an angle with respect to a plane defined by the plate, the angle being between about 30° and 60°.

According to an advantageous embodiment, the formation is a tab that is angled according to an angle between 30° and 60°, and having a hole for engaging the screw. The angled tab results from a cut out and a deformation of a portion of the plate.

In another embodiment, the formation is a hole angled at an angle between 30° and 60° for engaging the screw.

Considering the problem to be solved, the formation is located on a determined portion of the length of the plate so that the screw ensures the compression of the two bone parts.

BRIEF DESCRIPTION OF THE DRAWINGS

The invention is described hereinafter in more detail, with reference to the attached drawings in which.

DETAILED DESCRIPTION

Figure 1:
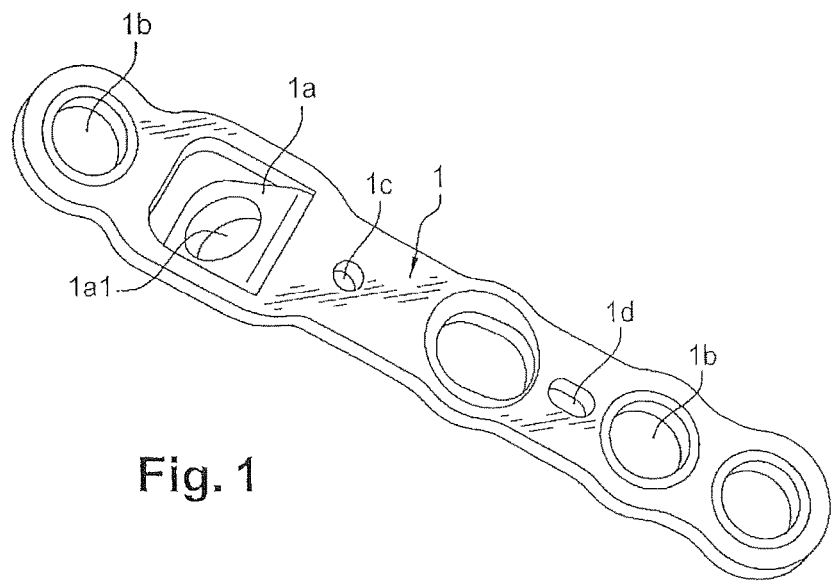
FIG. 1 is a perspective view of an embodiment of the plate.
Figure 2:
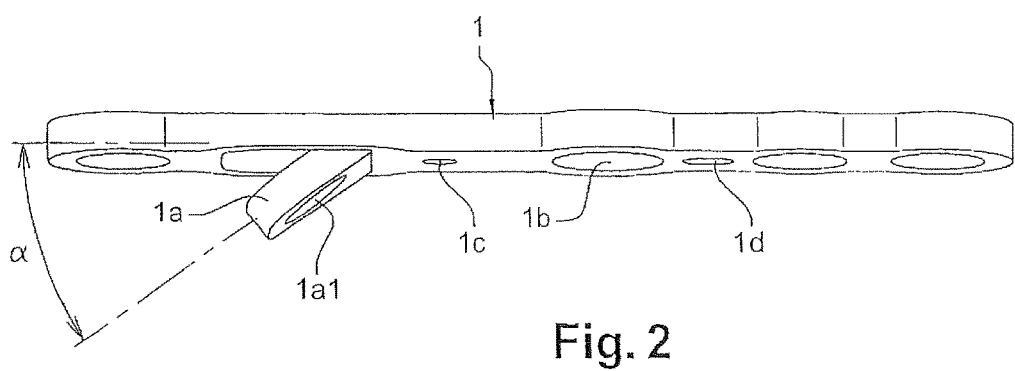
FIG. 2 is a side view of the plate.

According to the invention, the plate 1 has at least one formation 1a adapted to enable the positioning of at least one screw 2, at an angle α of between 30° and 60° with respect to a plane of the plate (FIG. 2).

In one embodiment, the formation 1a is an angled tab cut out and deformed from the plate. For example, the deformation is made with a cutting-punching operation. This angled tab has a hole 1a1 for screw 2. The angled tab 1a is positioned along the length of the plate so that after the screw 2 is fitted to it, the screw ensures the compression together of the two bone parts, as indicated below in the description.

In another embodiment, to allow for an angular orientation of the screw 2 according to an angle between about 30° and 60°, the formation 1a can be formed as an angled hole. It must be noted that the tab 1a enables adaptation of the angle as a function of the pathology to be treated, given that it is possible to deform this tab at will. In other words, the angle can be adjusted over a few degrees directly by the surgeon in the operating room, using an appropriate tool.

Figure 3:
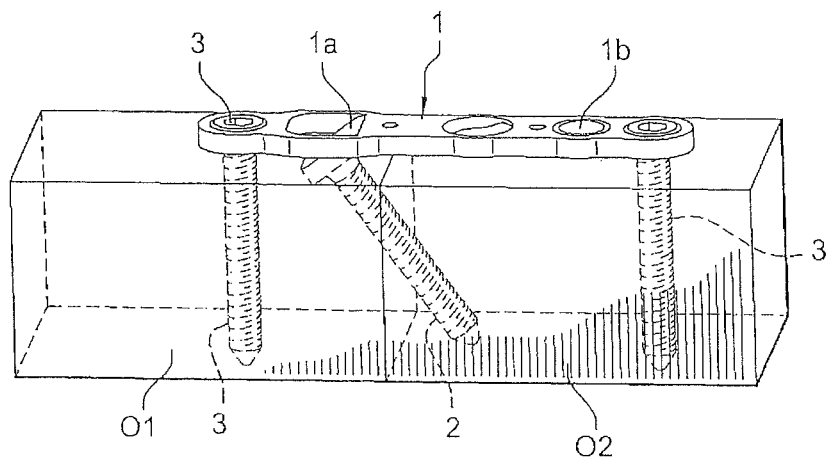
FIGS. 3 and 4 are perspective views showing the mounting of the plate between two bone parts and their orientation by means of the plate according to the invention, the bone parts being shown schematically.
Figure 4:
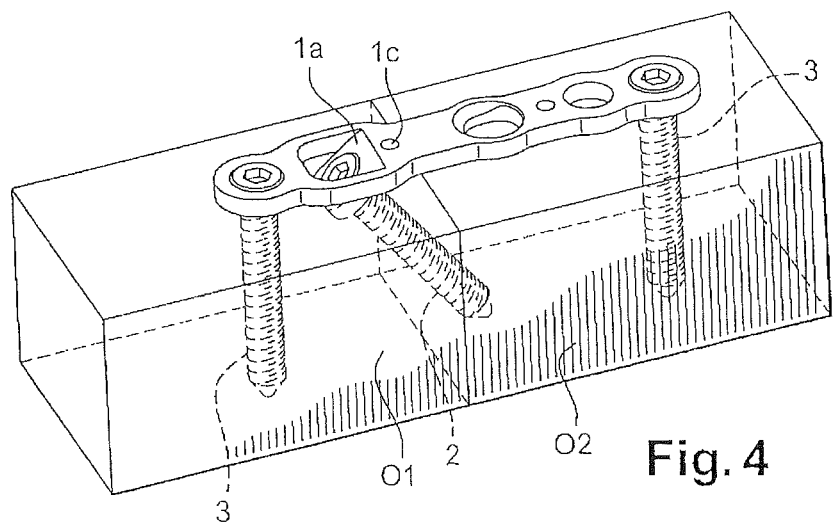

With reference to FIGS. 3 and 4 that show the positioning of the plate 1 between two bone parts O1 and O2:

Once the osteotomies have been carried out, a template of the plate, which does not have a guide formation, enables the position of the tab to be determined.

After determining the position of the tab, the surgeon makes a corresponding recess with the appropriate rasp.

Once the plate having the tab has been positioned, the surgeon sets one or two screws 3, on a side of the site of the osteosynthesis or the arthrodesis toward the tab. A temporary fastening pin can, possibly, be positioned in a complementary lug.

The screw 2 is then engaged in the hole 1a1 of the tab 1a to place the fracture in compression.

Once the compression has been done, the surgeon can screw one or several other additional fastening screws 3 and remove the temporary pin.

In a known manner, this plate 1 has smooth and/or threaded holes for the fastening screws 3 set in the bone parts O1 and O2 to engage in, as shown in FIGS. 3 and 4.

Similarly, the plate 1 can have at least one hole 1c for a pin for temporarily positioning the plate 1. Advantageously, the plate 1 can have a guide 1c for the insertion of a pin on the side of one of the bone parts O1 and another guide 1d for the insertion of another pin on the side of the other bone part O2.

Considering the effect of the desired compression, such as indicated above, the guide 1c is a circular hole whose diameter corresponds substantially to that of the pin, whereas the other guide 1d can be an elongated slot.

These provisions thus enable the bone to slide under the plate 1 as the screws are set, while ensuring compression along a precise direction, generally axially or parallel to the plate. The pins are of any known and appropriate type, and perfectly known to one having ordinary skill in the art.

The plate 1 can have several shapes, so that the holes 1a in particular can be aligned or arrayed, all or in part, according to the corners of a triangle or of a quadrilateral. These provisions, in triangle or in quadrilateral, of the screws, improve the stability of the mounting.

It must be noted also that the plate 1, no matter its shape, can be longitudinally bent so as to adapt to the curvature of the bone, consequently enabling the screws to form an angle between them.

The advantages are readily apparent from the description.

The invention claimed is:

1. A method of fusing bone parts comprising:
   (i) placing a bone plate across a fracture or a joint line between first and second bone parts, the bone plate including a first hole angled relative to the plate, a first pin hole, and a second pin hole, wherein an axis of the first hole crosses the fracture or joint line, the bone plate having a proximal surface and an opposite distal bone contacting surface, the first and second pin holes extending from the proximal surface to the distal surface;
   (ii) inserting a first guide pin through the first pin hole and into the first bone part so that the first guide pin fixes the bone plate relative to the first bone part;
   (iii) inserting a second guide pin through the second pin hole and into the second bone part;
   (iv) subsequent to steps (ii) and (iii), inserting a first bone screw having a screw head through the first hole, into the first bone part, across the fracture or joint line, and into the second bone part such that the entire screw head is below the proximal surface of the bone plate; and
   (v) compressing the first and second bone parts together and consequently causing the second guide pin to move from a first position inside the second pin hole to a second position.

2. The method of fusing bone parts as claimed in claim 1, wherein the first pin hole is circular and has a diameter corresponding substantially to a diameter of the first guide pin.

3. The method of fusing bone parts as claimed in claim 2, wherein the second pin hole is an elongate slot.

4. The method of fusing bone parts as claimed in claim 1, wherein the first hole is angled relative to the plate through a thickness of the plate.

5. The method of fusing bone parts as claimed in claim 4, wherein the first hole is angled by about between 30° and 60° relative to the plate.

6. The method of fusing bone parts as claimed in claim 1, further comprising inserting a second bone screw through a second hole in the plate and into the first bone part, and inserting a third bone screw through a third hole in the plate and into the second bone part, the second and third holes being locking holes.

7. The method of fusing bone parts as claimed in claim 6, wherein the second and third holes are threaded locking holes.

8. The method of fusing bone parts as claimed in claim 3, wherein the second pin hole has a width that corresponds substantially to a diameter of the second guide pin.

9. The method of fusing bone parts as claimed in claim 1, wherein the first hole is positioned on an extension of the plate, at least a portion of which is positioned below a bottom surface of the plate.

10. A method of fusing bone parts comprising:
    (i) placing a bone plate across a fracture or a joint line between first and second bone parts, the bone plate including a first hole angled relative to the plate, a first pin hole, and a second pin hole, wherein an axis of the first hole crosses the fracture or joint line;
    (ii) inserting a first guide pin through the first pin hole and into the first bone part so that the first guide pin fixes the bone plate relative to the first bone part;
    (iii) inserting a second guide pin through the second pin hole and into the second bone part;
    (iv) subsequent to steps (ii) and (iii), inserting a first bone screw through the first hole, into the first bone part, across the fracture or joint line, and into the second bone part;
    (v) compressing the first and second bone parts together and consequently causing the second guide pin to move from a first position inside the second pin hole to a second position; and
    inserting a second bone screw through a second hole in the plate and into the first bone part, and inserting a third bone screw through a third hole in the plate and into the second bone part, the second and third holes being locking holes, wherein the second and third holes are threaded locking holes,
    wherein the first hole is positioned on an extension of the plate, at least a portion of which is positioned below a bottom surface of the plate, wherein a fixation pathway extends through the plate above the extension and terminates at the first hole, and the method comprises inserting the first bone screw along the fixation pathway, through the first hole, into the first bone part, across the fracture or joint line, and into the second bone part.

11. A method of fusing bone parts comprising:
    (i) placing a bone plate across a fracture or a joint line between first and second bone parts, the bone plate including a first hole angled relative to the plate, a first pin hole, and a second pin hole, wherein an axis of the first hole crosses the fracture or joint line;
    (ii) inserting a first guide pin through the first pin hole and into the first bone part so that the first guide pin fixes the bone plate relative to the first bone part;
    (iii) inserting a second guide pin through the second pin hole and into the second bone part;
    (iv) subsequent to steps (ii) and (iii), inserting a first bone screw through the first hole, into the first bone part, across the fracture or joint line, and into the second bone part; and
    (v) compressing the first and second bone parts together and consequently causing the second guide pin to move from a first position inside the second pin hole to a second position,
    wherein the first pin hole is circular and has a diameter corresponding substantially to a diameter of the first guide pin, wherein the second pin hole is an elongate slot, wherein the second pin hole has a width that corresponds substantially to a diameter of the second guide pin, wherein the first hole is positioned on an extension of the plate, at least a portion of which is positioned below a bottom surface of the plate, wherein the extension is angled by about between 30° and 60° relative to the plate.

12. The method of fusing bone parts as claimed in claim 1, wherein the plate is curved so as to adapt to the curvature of at least one of the first and second bone parts, and the method further comprises inserting a second bone screw through a second hole in the plate and a third bone screw through a third hole in the plate so that the second and third bone screws are angled with respect to each other.

13. The method of fusing bone parts as claimed in claim 1, wherein movement of the second guide pin from its first position inside the second pin hole to its second position is caused via step (iv).

14. A method of fusing bone parts comprising:
    (i) placing a bone plate across a fracture or a joint line between first and second bone parts, the bone plate including a first hole angled relative to the plate, a first pin hole, and a second pin hole, wherein an axis of the first hole crosses the fracture or joint line, the bone plate having a proximal surface and an opposite distal bone contacting surface, the first and second pin holes extending from the proximal surface to the distal surface;

(ii) inserting a first guide pin through the first pin hole and into the first bone part so that the first guide pin fixes the bone plate relative to the first bone part;

(iii) inserting a second guide pin through the second pin hole and into the second bone part, the second pin hole being an elongate slot that has a width corresponding substantially to a diameter of the second guide pin;

(iv) subsequent to steps (ii) and (iii), inserting a first bone screw having a screw head through the first hole, into the first bone part, across the fracture or joint line, and into the second bone part such that the entire screw head is below the proximal surface of the bone plate; and (v) compressing the first and second bone parts together and consequently causing the second guide pin to move from a first position inside the second pin hole to a second position.

15. The method of fusing bone parts as claimed in claim 14, wherein the first pin hole is circular and has a diameter corresponding substantially to a diameter of the first guide pin.

16. The method of fusing bone parts as claimed in claim 14, wherein the plate includes a second hole having a diameter and the second pin hole has a length that is less than the diameter of the second hole.

17. The method of fusing bone parts as claimed in claim 14, wherein the first hole is angled relative to the plate through a thickness of the plate.

18. The method of fusing bone parts as claimed in claim 17, wherein the first hole is angled by about between 30° and 60° relative to the plate.

19. The method of fusing bone parts as claimed in claim 14, further comprising (vi) selecting an angle to insert the first bone screw across the fracture or joint line from amongst a plurality of different angles, and inserting the first bone screw along the selected angle through the first hole, into the first bone part, across the fracture or joint line, and into the second bone part.

20. The A method of fusing bone parts comprising:
(i) placing a bone plate across a fracture or a joint line between first and second bone parts, the bone plate including a first hole angled relative to the plate, a first pin hole, and a second pin hole, wherein an axis of the first hole crosses the fracture or joint line;
(ii) inserting a first guide pin through the first pin hole and into the first bone part so that the first guide pin fixes the bone plate relative to the first bone part;
(iii) inserting a second guide pin through the second pin hole and into the second bone part, the second pin hole being an elongate slot that has a width corresponding substantially to a diameter of the second guide pin;
(iv) subsequent to steps (ii) and (iii), inserting a first bone screw through the first hole, into the first bone part, across the fracture or joint line, and into the second bone part;

(v) compressing the first and second bone parts together and consequently causing the second guide pin to move from a first position inside the second pin hole to a second position; and
(vi) selecting an angle to insert the first bone screw across the fracture or joint line from amongst a plurality of different angles, and inserting the first bone screw along the selected angle through the first hole, into the first bone part, across the fracture or joint line, and into the second bone part,
wherein step (vi) includes deforming a tab of the plate to correspond to the selected angle.

21. The method of fusing bone parts as claimed in claim 14, wherein the first hole is positioned on an extension of the plate, at least a portion of which is positioned below a bottom surface of the plate, and wherein a fixation pathway extends through the plate above the extension and terminates at the first hole, and the method comprises inserting the first bone screw along the fixation pathway, through the first hole, into the first bone part, across the fracture or joint line, and into the second bone part.

22. An orthopedic implant comprising:
a plate having a length sufficient to span a fracture or joint of a patient, such that the plate is positionable alongside first and second bone parts straddling the fracture or joint, the plate including a first hole angled relative to the plate, the first hole having an axis that is configured to cross the fracture or joint during use, wherein the plate has a first pin hole that is circular and has a diameter corresponding substantially to a diameter of a first guide pin, and a second pin hole that is an elongate slot and has a width corresponding substantially to a diameter of a second guide pin, the plate having a proximal surface and an opposite distal bone contacting surface, the first and second pin holes extending from the proximal surface to the distal surface, and
a bone screw having a screw head, the bone screw configured to extend through the first hole and cross the fracture or joint during use such that the entire screw head is below the proximal surface of the plate.

23. The orthopedic implant as claimed in claim 22, wherein the plate includes a second hole having a diameter and the second pin hole has a length that is less than the diameter of the second hole.

24. The orthopedic implant as claimed in claim 22, wherein the first hole is angled by about between 30° and 60° relative to the plate.

25. The orthopedic implant as claimed in claim 22, wherein the first hole is positioned on an extension of the plate, at least a portion of which is positioned below a bottom surface of the plate, and wherein a fixation pathway extends through the plate above the extension and terminates at the first hole.

26. The orthopedic implant as claimed in claim 22, wherein the plate further comprises a second hole having an axis configured to extend only into the first bone part during use, and a third hole having an axis configured to extend only into the second bone part during use.

27. The orthopedic implant as claimed in claim 26, wherein the second and third holes are locking holes.

* * * * *